(12) United States Patent
Xu et al.

(10) Patent No.: US 7,992,999 B2
(45) Date of Patent: Aug. 9, 2011

(54) AUTOMATED ASSESSMENT OF OPTIC NERVE HEAD WITH SPECTRAL DOMAIN OPTICAL COHERENCE TOMOGRAPHY

(75) Inventors: Juan Xu, Monroeville, PA (US); Chaim-Gadi Wollstein, Pittsburgh, PA (US); Hiroshi Ishikawa, Pittsburgh, PA (US); Joel Steven Schuman, Pittsburgh, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 255 days.

(21) Appl. No.: 12/427,184

(22) Filed: Apr. 21, 2009

(65) Prior Publication Data

US 2009/0268159 A1    Oct. 29, 2009

Related U.S. Application Data

(60) Provisional application No. 61/071,347, filed on Apr. 23, 2008.

(51) Int. Cl.
*A61B 3/14* (2006.01)
(52) U.S. Cl. ........................... 351/206; 351/205
(58) Field of Classification Search .................. 351/201, 351/205, 206, 246
See application file for complete search history.

(56) References Cited

U.S. PATENT DOCUMENTS

| 6,735,331 | B1 * | 5/2004 | Binnun et al. ............. 382/133 |
| 7,524,061 | B2 * | 4/2009 | Yan et al. ................. 351/206 |
| 2006/0119858 | A1 | 6/2006 | Knighton et al. |

OTHER PUBLICATIONS

Juan Xu et al., "Automated Assessment of the Optic Nerve Head on Stereo Disc Photographs", Investigative Ophthalmology & Visual Science, Jun. 2008, vol. 48, No. 6, pp. 2512-2517.
Hiroshi Ishikawa et al., "Macular Segmentation with Optical Coherence Tomography", Investigative Ophthalmology & Visual Science, Jun. 2005, vol. 46, No. 6, pp. 2012-2017.
J. Xu, H. Ishikawa, G. Wollstein, K.R. Sung, J.S. Kim, V. Jurisic, L. Kagemann, R.A. Bilonick, M.L. Gabriele, K.A. Townsend, J.S. Schuman, *Automated Extraction of Optic Nerve Head Parameters from Spectral Domain Optical Coherence Tomography*, Poster No. 3659/D1049, presentation at ARVO 2008 Annual Meeting, Fort Lauderdale, FL (Apr. 29, 2008).
Juan Xu et al., "Automated Optic Disk Boundary Detection by Modified Active Contour Model", IEEE Transactions on Biomedical Engineering, vol. 54, No. 3, Mar. 2007, pp. 473-482.
S. Schuman, Carmen A. Puliafito, James G. Fujimoto, Optical Coherence Tomography of Ocular Diseases, 2nd ed. (Slack Inc., 2004).

* cited by examiner

*Primary Examiner* — Ricky L Mack
*Assistant Examiner* — Mahidere S Sahle
(74) *Attorney, Agent, or Firm* — Stephen A. Bent; Foley & Lardner LLP (57) ABSTRACT

A fully automated optic nerve head assessment system, based on spectral domain optical coherence tomography, provides essential disc parameters for clinical analysis, early detection, and monitoring of progression.

5 Claims, 10 Drawing Sheets
(1 of 10 Drawing Sheet(s) Filed in Color)

AUTOMATED ASSESSMENT OF OPTIC NERVE HEAD WITH SPECTRAL DOMAIN OPTICAL COHERENCE TOMOGRAPHY

RELATED PATENT APPLICATIONS

This application claims priority to U.S. Provisional Application Ser. No. 61/071,347, filed Apr. 23, 2008, which is incorporated by reference in its entirety.

STATEMENT REGARDING FEDERALLY SPONSORED RESEARCH

This invention was made with Government support under grant number RO1-EY013178-8, awarded by the National Institutes of Health. The government has certain rights in the invention.

BACKGROUND OF THE INVENTION

Glaucoma is a group of diseases of the eye characterized by progressive damage of the optic nerve that may result in visual field loss and eventual irreversible blindness if inadequately controlled. The World Health Organization currently ranks glaucoma as the second most common cause of blindness. As majority of patients do not experience any symptoms until the disease reaches an advanced stage, early detection and treatment is of utmost importance.

Figure 1:
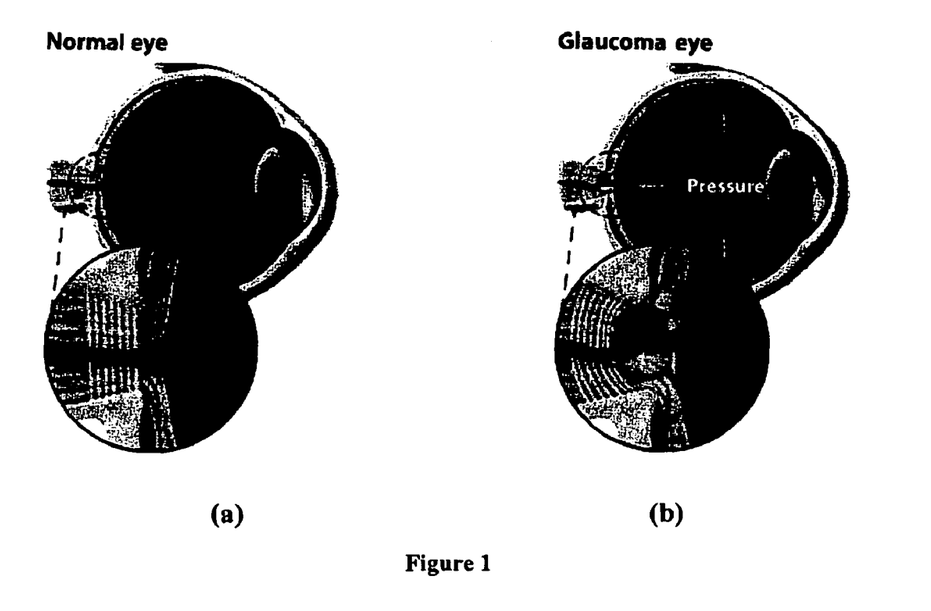
FIG. 1 illustrates the cross-sectional profile of the optic disc for a normal eye (a) and a glaucoma eye (b), respectively.
Figure 2:
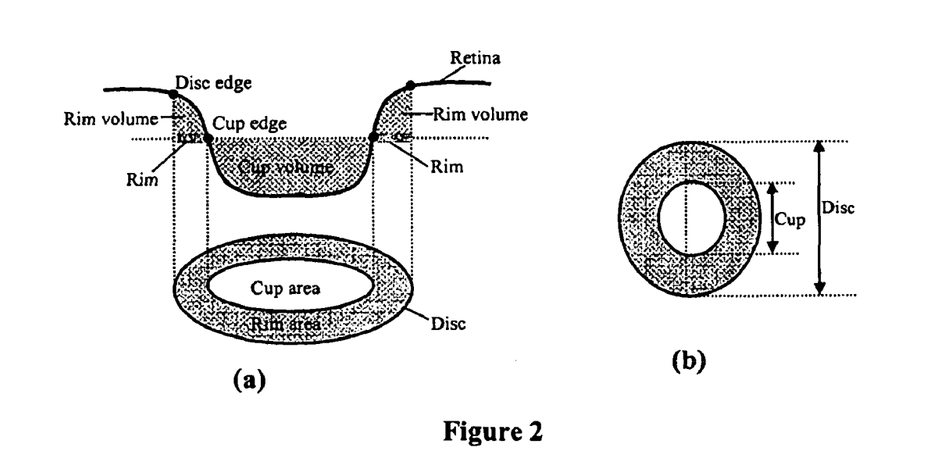
FIG. 2 depicts a geometric model of optic disc with a cross sectional profile, including disc parameters (a), and projected image (b), illustrating the determination of the vertical cup-to-disc (C/D) ratio.

The diagnosis of glaucoma is based on the appearance of the optic nerve head (ONH) and visual field, as shown in FIG. 1. Accordingly, there has been increasing interest in the development of imaging technology that can detect the structural changes at the level of the optic disc and in the retinal nerve fiber layer. Quantitative measurement of the cupping of the ONH is generally used to evaluate the progression of glaucoma. Certain features of the optic disc have been identified to correlate with such progression, such as rim area, cup area, and C/D area ratio (see FIG. 2).

Figure 3:
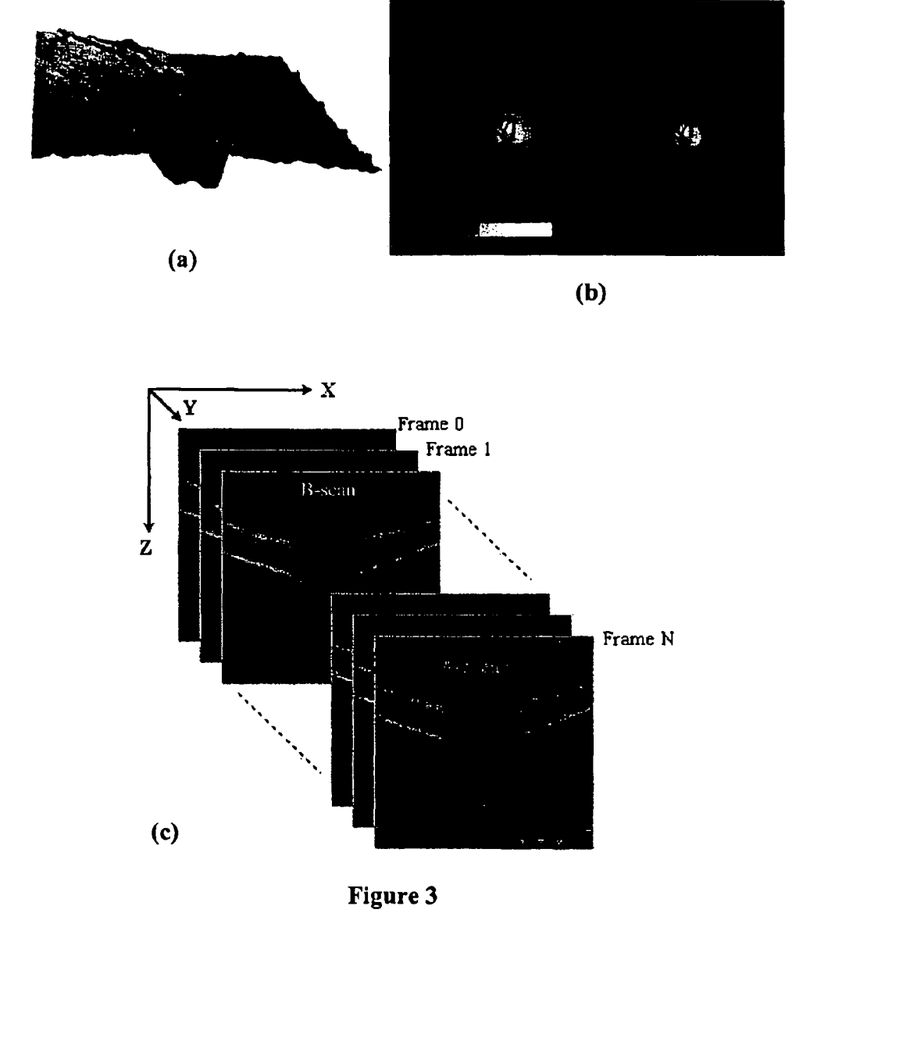
FIG. 3 presents different optic nerve head (ONH) perspectives: (a) a 3D topographical HRT image of the ONH; (b) stereo disc photographs of the ONH; and (c) a series (1, 2, ..., N) of "B-scans" of 3D spectral domain OCT image (3D cube image), each B-scan image representing a "frame." The coordinate system for the images and the direction of an "A-scan" are provided.
Figure 4:
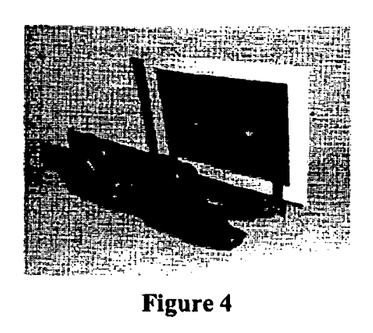
FIG. 4 is a photograph of a stereo viewer used to examine stereo disc photographs.

The conventional ophthalmic approaches to measuring three-dimensional (3D) structure and/or assessing ONH are Heidelberg Retina Tomography (HRT), stereo fundus camera imaging, and Optical Coherence Tomography (OCT), as shown in FIGS. 3(a)-3(c). HRT enables some of disc features to be objectively quantified, but it requires a manual delineation of the disc margin. This subjective definition leads to substantial inter-observer variability. Alternatively, disc photography is a common and cheap ophthalmic device widely used in fundus imaging for analysis and diagnosis. The assessment of the photographs is subjective and heavily dependent on the observer's skills, for instance, with using a stereo viewer (see FIG. 4).

Some studies have suggested automated methods to extract the disc parameters for analysis, but none of these methods has been commercialized. Moreover, the existing stereo disc photography could not get high resolution in depth due to the optical properties of cameras. And most importantly, depth information derived from stereo disc photos is mathematically calculated speculation rather than direct measurement.

Figure 5:
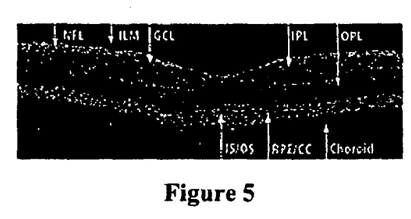
FIG. 5 illustrates one frame of a 3D OCT image, in which the organization of a retina is shown.

Spectral domain optical coherence tomography (SD-OCT) is a new high resolution imaging technique, capable of achieving micrometer resolution in depth. It allows detailed imaging of eye structures (see, e.g., FIG. 5). The introduction of 3D OCT, which can provide 3D image (cube image) of the ONH, offers a promising means for automated analysis, early detection and monitoring the progression of glaucoma and other optic nerve head diseases. There is no automated system to date to extract the ONH information with SD-OCT.

The present inventors developed an automated ONH detection/analysis based on conventional stereo optic disc photos, and they proved its usefulness and efficiency previously (see citation [3], infra). As described above, SD-OCT has a potential to replace conventional technique and to provide more detailed, 3D structural information about the ONH, relying on direct measurement and not on a mathematical theory. The aforementioned detection/analysis cannot be implemented for stereo disc photos, because the nature of the information captured by SD-OCT is quite different from that of stereo disc photos.

SUMMARY OF THE INVENTION

In view of the above-mentioned problems, the present inventors developed, pursuant to the invention described herein, a fully automated ONH assessment system based on SD-OCT, thereby providing important disc parameters for clinical analysis, early detection, and monitoring of progression. The system of the invention can provide subjective and reliable results automatically. The input data are from at least one 3D cube image, as provided by SD-OCT.

Figure 6:
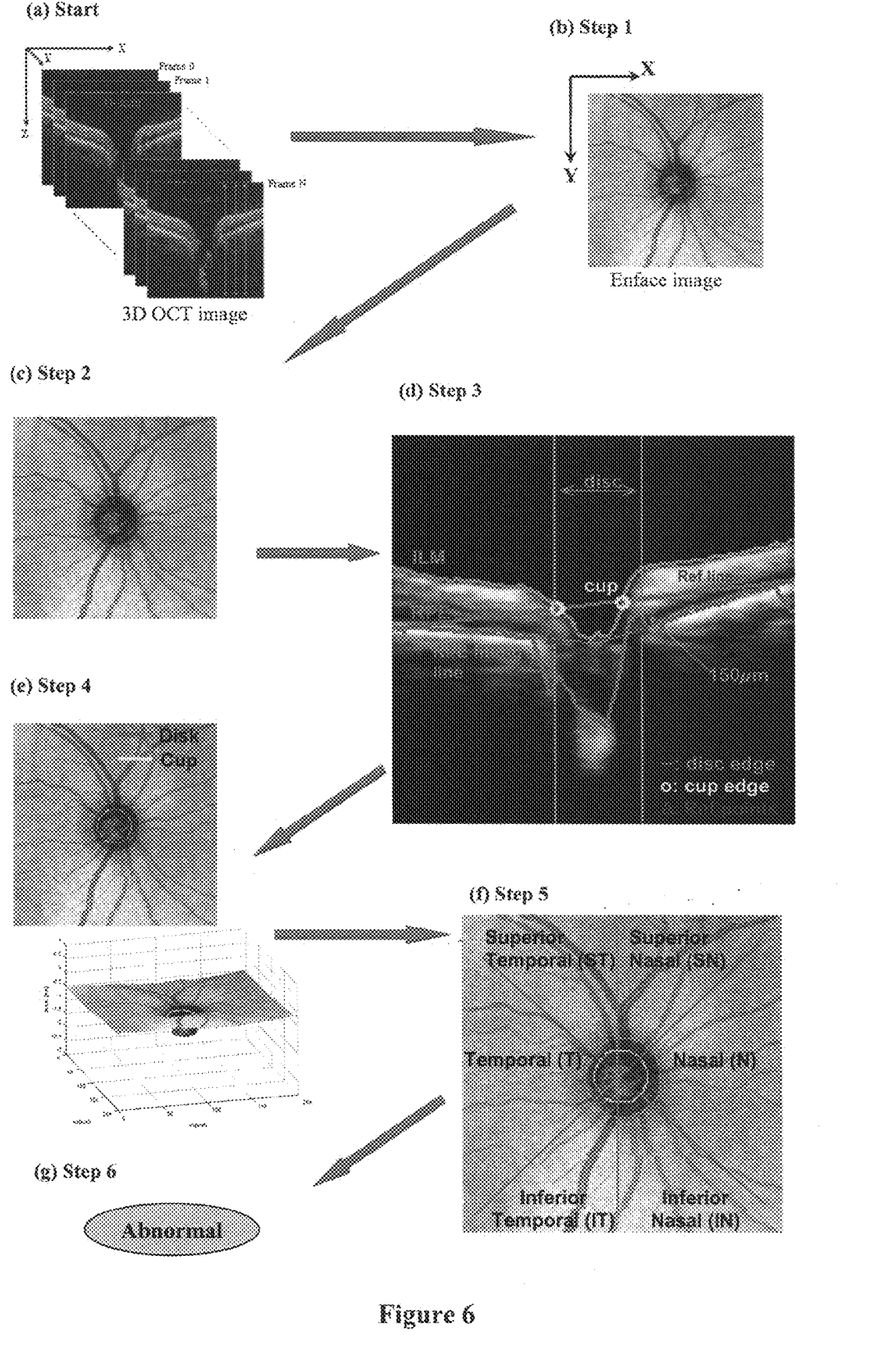

The overview of process flow, according to the invention, is provided in FIG. 6(a)-(g). The inventive process comprehends five steps:

1. Generate enface image (2D ONH image) by averaging the intensity values of each A-scan line. See FIG. 6(b).
2. Deformable model technique and unsupervised learning technique are applied on enface image to automatically detect the disc margin. See FIG. 6(c).
3. Automatically detect the internal limiting membrane (ILM) and retinal pigment epithelial (RPE) layers. See FIG. 6(d). The detected ILM layer is used to generate a 3D ONH surface from 3D-OCT cube image. A smoothed disc cupping, or "optic cup," or "cup," margin is estimated using the disc margin, the ONH surface and detected ILM and RPE layers. See FIG. 6(e).
4. Extract the ONH parameters, such as disc area, rim area, cup area, C/D area ratio, vertical C/D ratio, horizontal C/D ratio, rim volume, and cup volume for analysis and diagnosis. See FIG. 6(f).
5. Classify the given 3D ONH image as normal or abnormal. See FIG. 6(g).

In accordance with one aspect, therefore, the present invention provides a methodology for assessing status of a portion of a retina, which portion contains the optic disc, where the optic disc comprises the disc cupping. The methodology of the invention comprises:

(A) obtaining at least one enface image generated from a plurality of three-dimensional optical coherence tomographic image of the portion;

(B) generating a weighted edge map to delineate the margin of the optic disc in the enface image;

(C) in each image of the plurality, identifying spatial coordinates for the internal limiting membrane and the retinal pigment epithelium layer in the optic disc; then (D) generating at least one three-dimensional surface image of the optic disc from the enface image, wherein depth in the image corresponds to the spatial coordinates of the internal limiting membrane;

(E) obtaining at least one of (i) reference points, (ii) a reference line, and (iii) a reference plane with respect to at least one of (1) the retinal pigment epithelium layer and (2) said margin of the optic disc from each image of said plurality or said three-dimensional surface image; then (F) using said reference line or reference plane to delineate the margin of the disc cupping in said surface image; then (G) determining shape information of the portion from the surface image; and, from the shape information;

(H) generating at least one three-dimensional point distribution model to classify the portion with respect to predetermined values that reflect retinal status.

According to another aspect of the invention, a program is provided that makes an information processing apparatus, such as a computer, execute a method as described above. In a preferred embodiment, such apparatus is a part of or integral to an imaging instrument. Illustrative of such an imaging instrument is a medical imaging instrument, including an optical tomography instrument.

The present invention further encompasses, in another of its aspects, a computer-readable recording medium that comprises a program as mentioned above.

BRIEF DESCRIPTION OF THE DRAWINGS

The application contains at least one drawing executed in color. Copies of this patent or patent application publication with color drawing(s) will be provided by the Office upon request and payment of the necessary fee.

FIG. 6 is a graphic overview of process flow according in one embodiment of the invention. At the beginning (a), a series of B-scans of the 3D OCT image are taken. In the first step (b), an enface image is generated by averaging the intensity values of each A-scan line from of the 3D OCT images. In the second step (c), the disc margin on the enface image is detected. In this embodiment, to effect segmentation of the ILM and the RPE layer in the third step (d), reference points are detected and a reference line subsequently is generated. The cup margin points also can be detected via the reference line and the ILM layer profile. In the fourth step e), the overall cup margin profile (and/or the disk profile) thus obtained can be further smoothed or refined by a suitable algorithm. The ONH parameters can be extracted from the profile in a fifth step (f) and, in a sixth step (g), the observed sample can be classified as "normal" or "abnormal," based on the extracted ONH parameters.

DETAILED DESCRIPTION OF THE INVENTION

All the references mentioned herein are incorporated by reference in their entirety. As noted above, the overall system of the present invention is diagramed schematically in FIGS. 6(a)-6(g). A detailed description of the procedures is given as follows:

1. Generate enface image (2D ONH image) from the 3D OCT image taken from SD-OCT, as shown in FIG. 6(a) and/or FIG. 3(c):

(a) The enface image is generated by averaging the intensity values of each A-scan line.

(b) The intensity values is normalized to obtain a high contract enface image.

Step 1, generation of enface image, comports with existing methodology (FIG. 6(b)). The current SD-OCT machines of several different brands already have implemented enface image generation, based on this basic idea [5]. Data can be utilized from different modes of scanning protocols, such as A-scan, B-scan, and C-scan.

2. Detect the disc margin on 2D ONH image (FIG. 6(c))

Automated detection of disc margin is a challenge due to the blood vessel occlusion on the disc margin. OCT enface image is a grey scale image derived from 3D OCT data with low resolution and high noise, which makes the disc margin detection difficult. Moreover, peripapillary atrophy (having high reflection on the 3D OCT image and thus a high intensity level on the enface image) often can be a problem, reducing the performance of the disc margin detection algorithm.

In the present invention, the weighted edge map is computed to detect the initial disc margin, which efficiently solves the problem of peripapillary atrophy, while clustering and smoothing updates are integrated in the traditional active contour model algorithm to let the algorithm robust to the blood vessel occlusion. All the aspects of the present invention directed to automated assessment, such as the computation of parameters and the processing of images as described throughout this disclosure, can be carried out with a suitable algorithm in any format, such as one written and executable in MATLAB, C, C++, or another publicly available programming language.

Figure 7:
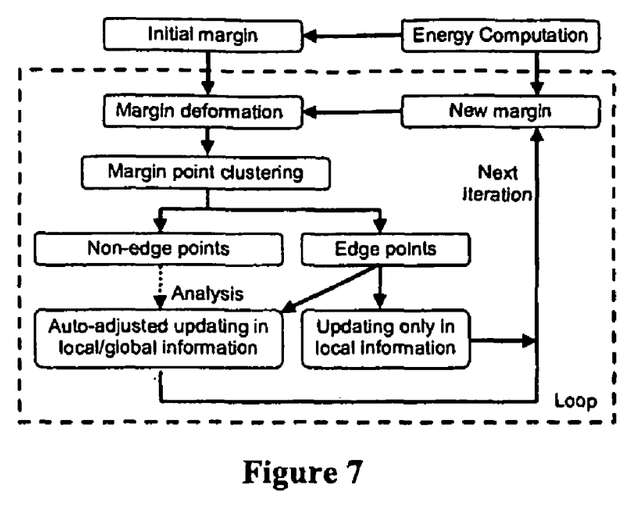
FIG. 7 presents a flowchart of a process, according to Xu et al., 2007 (citation [1]), for detecting the disc margin.
Figure 8:
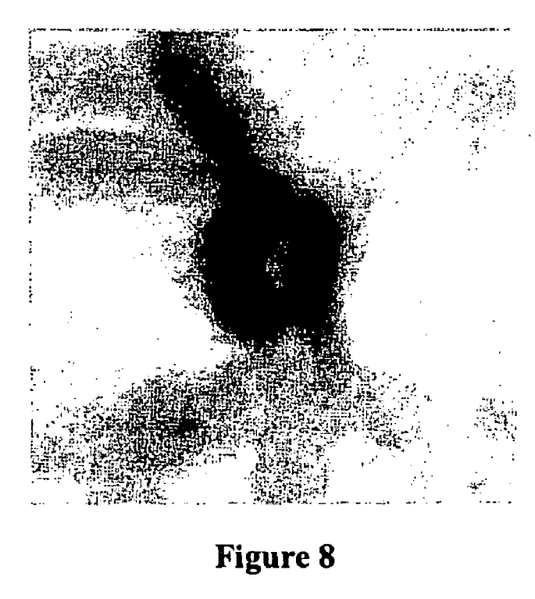
FIG. 8 is an enface image showing a region of an ONH, which region has been selected as the candidate region pursuant to the invention. A median filter can be applied to the enface image to blur the image, whereby pixels with 5% lowest intensity value are selected as the candidate region of the ONH. The centroid of the selected pixels is set to be the initial disc center, which is marked with "+."

A modified active contour model, including several steps, is used to detect the disc margin: (a) initialize candidate disc region and disc center, (b) compute the initial disc margin points (c) define the energy function for margin deform (d) set the weight of energy function (e) deform the disc margin by searching a location with minimization energy, (f) classify the margin points into edge point or non-edge points, (g) update and smooth the disc margin, and then (h) repeat steps (e) to (g) until the disc margin does not change. FIG. 7 presents an overall procedure for disc margin detection, pursuant to one embodiment of the invention. Details can be summarized as follows:

(a) Median filter can be applied to the enface image to blur the image. Pixels with 5% lowest intensity value are selected as the candidate region of the ONH. The centroid of the selected pixels is set to be the initial disc center. (FIG. 8)

(b) An edge map is generated by Canny edge detection with Gaussian smoothing. A weight for each edge pixel is set linearly inversely proportional to the intensity value of this pixel. Therefore, the edge pixels on the peripapillary atrophy almost always have low weight since the peripapillary atrophy has high intensity value. The disc center and radius are detected by Circular Hough transform, based on the weighted edge map, where the searching window is limited at a certain range around the initial disc center. The initial disc margin is set to be a circle based on the detected disc center and radius (see FIG. 9).

(c) Local energy is computed for each margin point for margin deform. Energy function includes both the internal energy and external energy. The absolute values of the first and second derivatives can be set to be the internal energy. The external energy can comprise three terms: the magnitude of gradient, the difference between the gradient orientation and the radial angle to the disc center, and the difference of the intensity value of the given pixel to the average intensity value of all the disc margin points. [1]

(d) Let the $\alpha_1$ to $\alpha_5$ denote the weights of two internal energy terms and three external energy terms, i.e., $\alpha_1$ for first derivative term, $\alpha_2$ for the second derivative term, $\alpha_3$ for the magnitude of gradient term, $\alpha_4$ for the gradient orientation term, $\alpha_5$ for the intensity level term. Based on the testing results, $\alpha_1:\alpha_2:\alpha_3:\alpha_4:\alpha_5$ is set to be 1:0.5:1:0.7:0.7.

Figure 9:
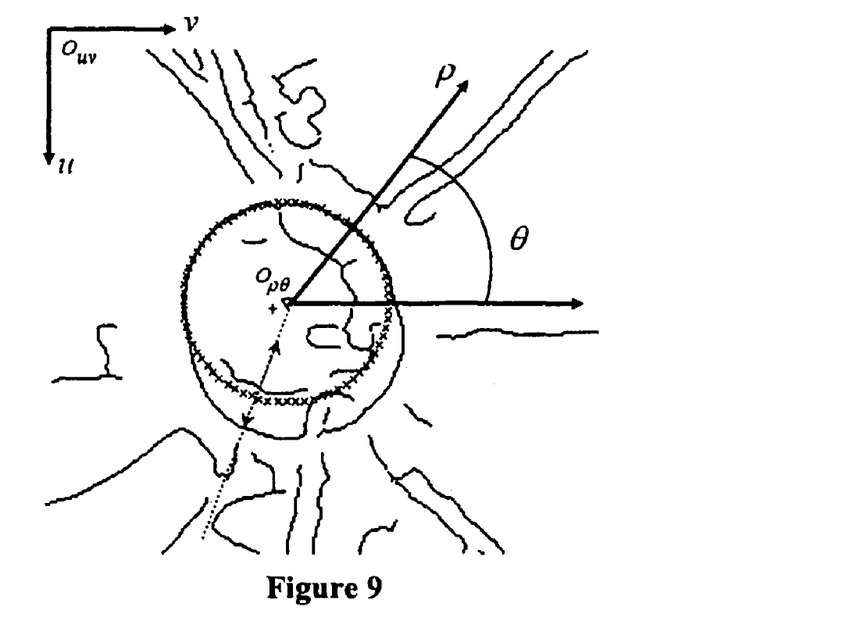
FIG. 9 shows an edge map for the Circular Hough transform. Solid lines in the figure represent the edges; '+' initial disc center $c_0$; '∇'—disc center $\bar{c}_0$ computed from the Circular Hough transform; 'x' initially circular disc margin points based on center $\bar{c}_0$ and radius $\bar{r}$ computed from the Circular Hough transform; arrow dash line is the deforming range. See citation [1], infra.
Figure 10:
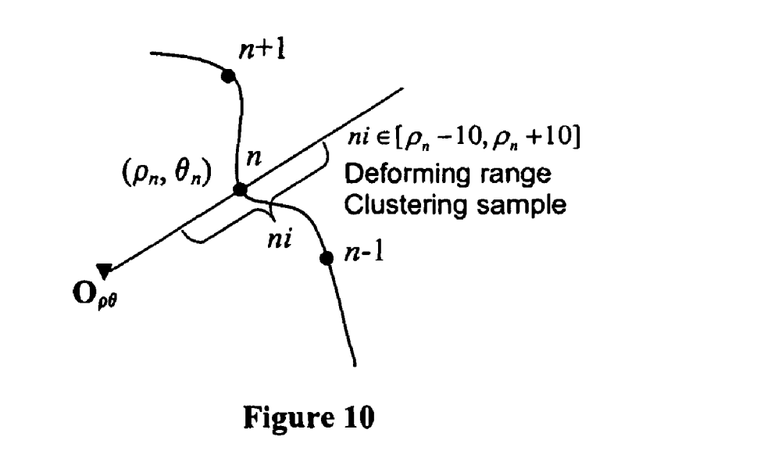
FIG. 10 depicts the range of disc margin deformation, where the margin deforms to the location with the minimal energy, and illustrates a clustering sample in the technique of "clustering" (see citation [1]).

(e) The disc margin deforms to the location with the minimal energy, as shown in FIG. 10 and the arrow line in FIG. 9.

Figure 11:
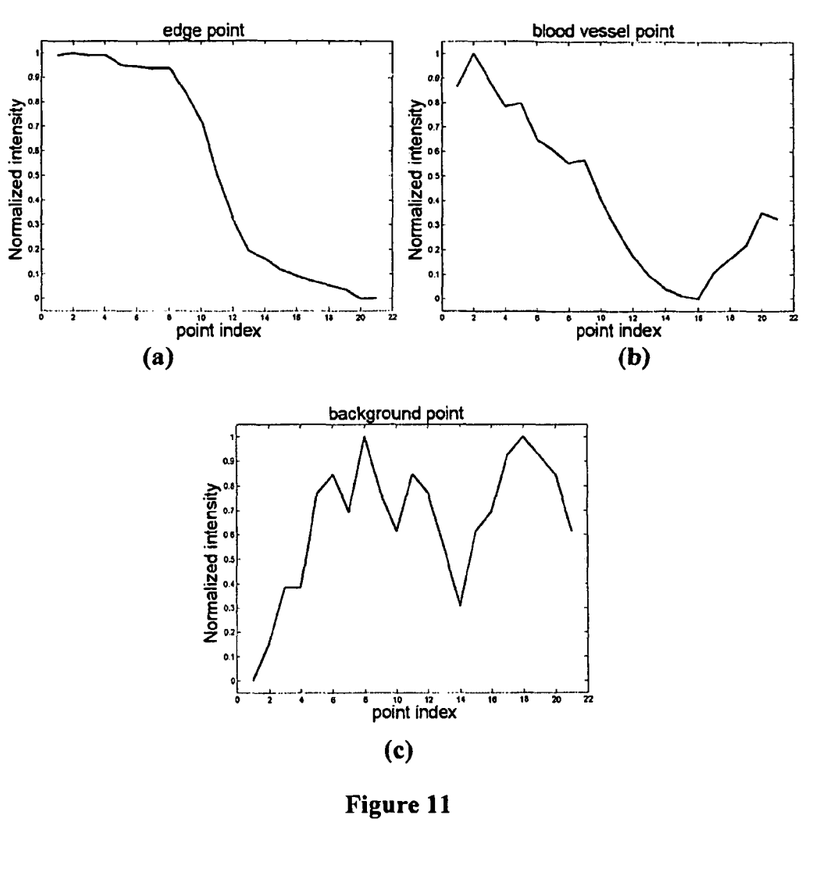
FIG. 11 presents normalized clustering samples, from citation [1], for a contour point that is located (a) on the disc edge (an "edge point"); (b) on the blood vessel (a "blood vessel point"); and (c) in the background (a "background point"), respectively, on the enface image.

(f) The profile of each margin point is generated along radial direction, as shown in FIG. 10. The points on disc edge, vessel, and in the background can have different profiles, as illustrated in FIGS. 11(a)-11(c). The margin points are roughly classified into edge points or non-edge points by weighted clustering algorithm [1]. One example of the classification result is given in FIG. 12.

Figure 12:
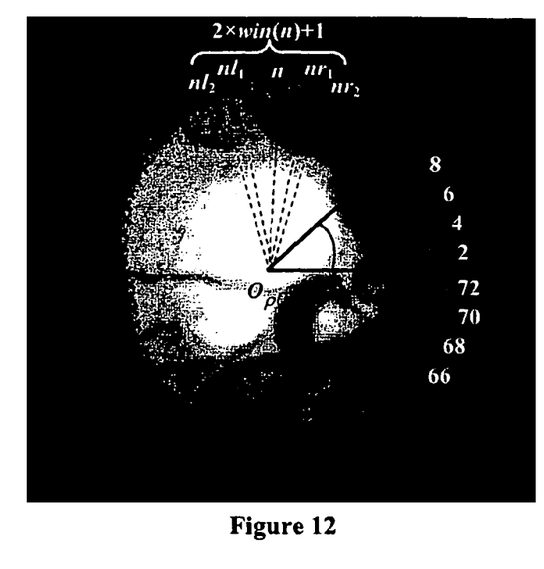
FIG. 12 shows clustered contour points used during the smoothing update process, from citation [1]; 'x' represents the edge points and 'o' represents the possible non-edge points.

(g) The margin points are updated and smoothed with the auto-adjusted window using the edge points only [1], as shown in FIG. 12, in which point n is updated by averaging of points $nl_1$, $nl_2$, n, $nr_1$, $nr_2$.

(h) Steps (e) to (g) are repeated until the margin does not change. [1]

A disc boundary detection algorithm on the fundus photograph was published in [1]. In accordance with the present invention, the algorithm can be modified to detect the disc margin on the enface image. As provided in Table 1, there are several differences in the algorithm of the present invention from the published algorithm.

One important difference may be in step (b), as shown in Table 1. The weighted edge map is generated to compute the initial disc margin. Peripapillary atrophy comes mostly in the enface image. Almost all of the cases with peripapillary atrophy lead to failures of the algorithm. Accordingly, it can be very desirable that the present invention solves this problem.

The peripapillary atrophy has a different appearance, compared to the background of retinal surface. Removing the effect of the peripapillary atrophy therefore has been problematic. By observation, the peripapillary almost always has a high intensity value. Introducing weight into the edge map based on the intensity value can solve this problem efficiently, pursuant to the invention, and greatly improves the performance of the algorithm.

TABLE 1

Comparison of the disc margin detection algorithms between present invention and previous publication

| | Invention | Publication [1] |
|---|---|---|
| Step 2(a) initial disc region | 5% lowest intensity value | 13% highest intensity value |
| Step 2(b) initial disc margin | Weighted edge map | Edge map |
| Step 2(d) energy weight setting | 1:0.5:1:0.7:0.7 | 1:0.1:1.2:1:1 |

Step 2, disc margin detection can be performed any suitable method. For example, in one embodiment of this invention, the method can be a methodology modified from that described in publication [1]. The modifications (Step 2(a), (b), (d)) are enumerated in Table 1. Weight edge mapping can be used to initialize the circular disc margin points. This modification efficiently solves the peripapillary atrophy problem.

3. Estimate the cup margin on 3-D ONH image

In one embodiment, two cup margin points are detected on each frame inside the disc margin. The cup margin is generated by smoothing the overall detected cup margin points.

(a) The spatial coordinates of the internal limiting membrane ("ILM") and retinal pigment epithelium ("RPE") are automatically detected by searching for the peaks of each A-scan line on the 3D OCT image. [2]

(b) A 3D surface image of the ONH (3D ONH model) is created from detected ILM layer.

(c) On each frame, reference points can be obtained from segmentation of the RPE layer, and these references points can be subsequently used to obtain a reference line and/or a reference plane. Segmentation can be effected via a published method [2]. In one embodiment, the RPE layer on the left side of the left disc margin (a "first segment") and right side of the right disc margin (a "second segment") are fitted to two straight lines. The first segment and the second segment of the RPE layer in each image are fitted with two straight lines, respectively, which lines intersect the margin of the optic disc in each image.

(d) Two points of cup edge are detected frame by frame as the cross points of the ONH surface and the reference line and/or plane. The reference line and/or plane can be obtained from reference points. In one embodiment, the cross points, or intersects, of two fitting lines with the left and right disc margins are detected as the reference points. Other types of reference points can also be used. A reference line or reference plane can be generated at a location, relative to the retina, anterior to the two reference points. In one embodiment, the location can be between about 100 microns and 200 microns, such as 150 microns.

(e) The centroid of all cup margin points is computed as the cup center. The cup margin points are transferred into a polar coordinate system at the cup center. Any suitable smoothing techniques can be applied to the delineated cup margin. Such technique can include a mean filter, a Gaussian filter, and a median filter. In one embodiment, a 1D median filter is applied on the radiuses of the cup margin points to exclude the outliers. The final cup margin is generated by cubic interpolation on the smoothed cup margin points.

Alternatively, steps (c) and (d) can be performed differently. In one alternative embodiment, segmentations of the RPE layer using fitting is not used, and the coordinates information (e.g., pixel location) of the intersects between the optic disc margin and the RPE layer as is in each frame are considered as the reference points. Reference lines can then be generated from the reference points.

In another embodiment, no reference points or lines are generated. Instead, a reference plane is generated based on the optic disc margin as detected on the 3D surface image. The reference plane can be generated at a location arbitrarily chosen relative to the ILM layer, as shown in FIG. 6(e). For example, the reference plane can be generated at a depth between about 100 microns and 200 microns, such as 150 microns, relative to the ILM layer.

Figure 13:
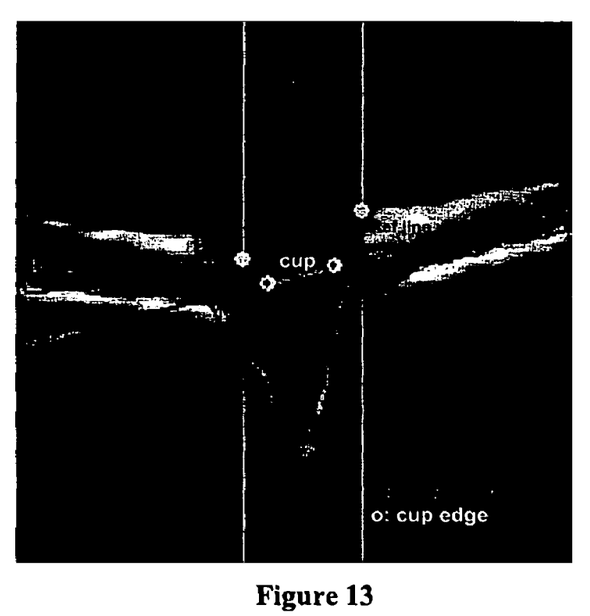
FIG. 13 illustrates the use of end points of RPE as the reference points, where the RPE is concave in the ONH region.

Step 3, cup margin detection (see FIG. 6(d)), can employ a methodology adapted from published principles [4], but any suitable method can be used. Previously, the endpoints of RPE are used as the reference points to generate the reference line located at 150 microns anterior to the two reference points [4]. The RPE ends may be blocked by the shadow of a blood vessel, however, and also the RPE may be concave in ONH region in some cases (FIG. 13), making the detection of reference points unreliable.

It has been a problem heretofore how to generate reliable reference points for cup margin detection. The present invention provides an approach to computing such reference points, using the fitting lines (Step 3(c)). The invention thus solves this problem in a manner that is robust to vessel shadow and concave RPE.

Step 3(a) segmentation, such as that of retina, can be the published method [2]. Step 3(b) and Step 3(d), generation of ILM surface and reference line, can embody the basic ideas of cup margin detection used in OCT [4]. New to this invention are various embodiments of the detection of reference points, reference line, and/or reference plane as provided in step 3(c), and the use thereof in step 3(d), and the overall smoothing the cup margin in step 3(e).

4. Calculate ONH parameters through the 3D ONH model, disc and cup margins to quantify the structure of ONH
   (a) Compute disc, rim and cup areas
   (b) Compute C/D area ratio and R/D area ratio
   (c) Separate the disc into six sectors; compute C/D area ratio and R/D area ratio in each sector.
   (d) Detect the physical centers of the disc and cup; measure the vertical diameters of disc and cup through the physical centers; compute the vertical C/D ratio; measure the horizontal diameters of disc and cup through the physical centers; compute the horizontal C/D ratio.
   (e) Count the voxels inside the cupping; convert it into cup volume
   (f) Count the voxels between the cup surface and the ONH surface within the disc margin, convert it into rim volume.
   (g) Measure the slope of neuroretinal rim at each predetermined angle through the disc center.

All the disc parameters described above are the common information used by doctors in the diagnosis of glaucoma.

Step 4, ONH qualification ((see FIG. 6(f)), is grounded in the basic idea of ONH analysis [4]. The ONH parameters measured in one embodiment are the traditional parameters for ONH evaluation.

5. Classify the given ONH image (see FIG. 6(g))

Accurately classifying of the given ONH image as a normal or abnormal image can be a challenge. Because the information of the entire 3D ONH structure is not previously available, only the simple measurements or simple combination of the measurements of ONH parameters are used to roughly classify the normal and abnormal image. For example, glaucoma should be considered if the C/D area ratio is larger than 0.6. This simple computation can be insufficiently accurate, however.

In an embodiment of the invention, the 3D point distribution model can be first applied in the classification, with all the ONH shape information used in classification instead of the simple ONH parameters. The shape information can comprise at least one of the conventional ONH parameters used by medical practitioners and the parameters from the 3D point distribution model. Therefore, more information can be obtained from the training process, which in turn can improve the classification accuracy.

The present invention uses various 3D ONH shape information to classify a given sample. Therefore the classification can be more accurate than only using the ONH parameters. In addition, the shape information can be obtained from the portion of tissue within the disc margin from a 3D surface image. The overall 3D ONH surfaces of the training samples are used to generate a 3D point distribution model (PDM) in shape space. Eigenvectors of the training set can be computed to represent the normal and abnormal datasets. The given 3D ONH image can be transferred into the shape space and represented by the mean and eigenvectors of each training set. The energies to the two training sets can be computed. The given sample can be classified into the group, which has smaller energy.

Figure 14:
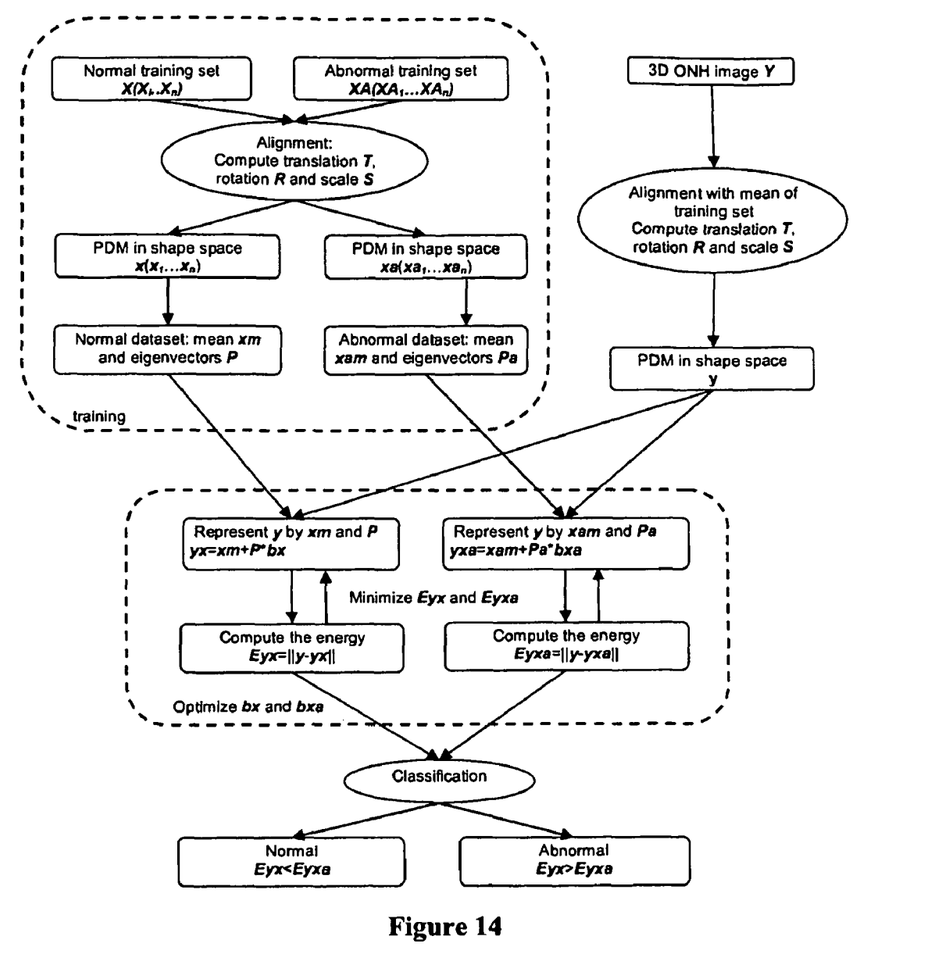
FIG. 14 is a flowchart block diagram, which illustrates a classification process of the invention based on an evaluation of a minimized energy function (PDM-Point distribution model) with respect to a 3D ONH image.

The procedure is depicted in the block diagram as shown in FIG. 14. An illustrative description also can be found in [6], which is incorporated here by reference in its entirety. Details are described as follows:

(a) Normal dataset $X(X_1, X_2, \ldots X_n)$ and abnormal dataset $XA(XA_1, XA_2, \ldots XA_n)$ are subjectively selected as the training samples.

(b) Randomly selecting one sample from the training set as the reference, the 3D ONH images (including both normal and abnormal samples) are aligned with the reference by optimizing the translation T, rotation R and scale S on the enface image to get the same disc center and disc size. The overall ONH surface is normalized horizontally by projecting the disc margin in the horizontal direction. 3D ONH point distribution models $x(x_1, x_2, \ldots x_n, xa_1, xa_2, \ldots xa_n)$ are generated in the shape space for all the aligned samples in the training set using the location of normalized ONH surface (ILM location in z-axis).

(c) The covariance matrices for the normal and abnormal datasets are computed, and then mean (xm for normal dataset, xam for abnormal dataset), eigenvectors (P for normal dataset, Pa for abnormal dataset) and eigenvalues of each dataset are computed. Each training sample can be represented by the mean and linear combination of the eigenvectors.

(d) Given a new sample Y (an ONH image with detected disc margin and 3D ONH surface), the alignment parameters of translation, rotation and scale are optimized by minimizing the mean of the disc margins of all the training samples with the given sample to get the same disc center and disc size. The ONH surface is normalized horizontally by projecting the disc margin in the horizontal direction.

(e) A 3D ONH point distribution model y in the shape space is generated from the aligned sample. The given sample is also represented by the mean and eigenvectors of each training dataset, written as yx=xm+P*bx for normal dataset, yxa=xma+Pa*bxa for abnormal dataset, where bx and bxa are the weights of the eigenvectors.

(f) The energy to each training dataset in shape space is defined as the difference between the original sample y and represented point distribution models yx and yxa, as Eyx=∥y−yx∥ and Eyxa=∥y−yxa∥.

(g) Given the initial bx and bxa, repeat steps (e) and (f) to optimize the bx and bxa by minimizing the energies Eyx and Eyxa.

(h) The given ONH image is labeled to the class, which has the smaller energy.

(i) The local classification can be done by separating the disc into six sectors and labeling the ONH image as normal or abnormal locally in each sector using the same computation.

Step 5, ONH classification using a 3D point distribution model: Overall 3D shape information of ONH is used for classification, which can make the algorithm more accurate than merely using the simple ONH parameters. The original 3D image can be transferred into the shape space and represented by eigenvectors. This process can extract the major components (eigenvectors corresponding to large eigenvalues) from training set and ignores minor components, in order to improve the classification accuracy.

Compared to HRT and stereo photography, the different features and techniques of the present invention include:

1. In this invention, not only retinal surface but also different retinal layers can be presented, quantified, and analyzed. No such information is provided by HRT (see, e.g., FIG. 3(a)) and disc photography, where only retinal surface profiles are available.
2. This invention uses the developed software and techniques (retina segmentation techniques) to generate a 3D ONH model from a 3D OCT cube image, as opposed to the HRT confocal scanning laser opthalmoscope (CSLO) imaging technique to generate a pseudo 3D image (ONH topography image). Matching technique or manual observation is used in stereo disc photography to obtain 3D ONH model (see, e.g., FIG. 3(b)).
3. This invention uses automated method to extract the disc margin, as opposed to manually drawing or modifying the disc margin by technicians in HRT and disc photography.
4. In this invention, the cup margin is extracted at the cross points of a reference line and/or a reference plane and detected retinal surface. Cup points can be detected frame by frame and then smoothed. HRT measures the cup margin by using a fixed offset parallel plane from the reference plane. In some studies of disc photographs, the cup margin is extracted by using the combined information of depth, smoothness, shape and location.

More than 60 images have been tested. One exemplary image is shown in FIG. 6. Fully automated ONH assessment with SD-OCT was found to perform as well as human experts in quantification of disc parameters. Additional statistics determination can be performed to evaluate the performance of the assessment against the results by human experts. The present invention thus can provide an objective and reliable option to quantitatively evaluate, analyze, and monitor the structural changes of ONH, using the high-resolution imaging technique, SD-OCT.

The present invention has substantial commercial potential in various applications. It can be used clinically by eye care professionals as well as for research purposes. The method can be automated by a software program executable by an information process apparatus, such as a computer. The information process apparatus can be a part of an instrument, such as a medical device, including an imaging instrument, such as a medical imaging instrument, including an optical tomography instrument. The optical tomography instrument can be any type of optical tomography instrument, such as a two-dimensional, three-dimensional, time-domain, or spectral-domain optical tomography instrument. In one embodiment, a program that can execute the presently claimed method is recorded on a computer-readable recording medium, such as a compact disc (CD), floppy diskette, or DVD.

The present invention is described above with respect to various illustrative embodiments and specific aspects. It is to be understood, however, that the invention should be delineated in scope only by the following claim.

CITATIONS

[1] Juan Xu, Opas Chutatape, and Paul Chew, "Automated Optic Disk Boundary Detection by Modified Active Contour Model," *IEEE Transactions on Biomedical Engineering* 54: 473-82 (2007).
[2] Hiroshi Ishikawa, Daniel M. Stein, Gadi Wollstein, Siobahn Beaton, James G. Fujimoto, and Joel S. Schuman, "Macular Segmentation with Optical Coherence Tomography," *Investigative Opthalmology and Visual Science* 46: 2012-17 (2005).
[3] Juan Xu, Hiroshi Ishikawa, Gadi Wollstein, Rick Bilonick, Kyung R Sung, Larry Kagemann, Kelly A Townsend, and Joel S. Schuman, "Automated Assessment of Optic Nerve Head on Stereo Disc Photographs," *Investigative Opthalmology and Visual Science* 49: 2512-2517 (2008).
[4] S. Schuman, Carmen A. Puliafito, James G. Fujimoto, OPTICAL COHERENCE TOMOGRAPHY OF OCULAR DISEASES, 2nd ed. (Slack Inc., 2004).
[5] Robert W. Knighton, Shuliang Jiao, Govanni Gregori, and Carmen A. Puliafito, "Enhanced optical coherence tomography for anatomical mapping," U.S. patent application 2006/0119858.
[6] J. Xu, H. Ishikawa, G. Wollstein, K. R. Sung, J. S. Kim, V. Jurisic, L. Kagemann, R. A. Bilonick, M. L. Gabriele, K. A. Townsend, J. S. Schuman, *Automated Extraction of Optic Nerve Head Parameters from Spectral Domain Optical Coherence Tomography*, Poster No. 3659/D1049, presentation at ARVO 2008 Annual Meeting, Fort Lauderdale, Fla. (29 Apr. 2008).

What is claimed:
1. A method of assessing status of a portion of a retina, which portion contains the optic disc, wherein said optic disc comprises the disc cupping, said method comprising the steps of:
(A) obtaining at least one enface image generated from a plurality of three-dimensional optical coherence tomographic images of said portion;
(B) generating a weighted edge map to delineate the margin of the optic disc in said enface image;

(C) in each image of said plurality, identifying spatial coordinates for the internal limiting membrane and the retinal pigment epithelium layer in the optic disc; then (D) generating at least one three-dimensional surface image of the optic disc from said enface image, wherein depth in said image corresponds to said spatial coordinates of the internal limiting membrane;

(E) obtaining at least one of (i) reference points, (ii) a reference line, and (iii) a reference plane with respect to at least one of (1) the retinal pigment epithelium layer and (2) said margin of the optic disc from each image of said plurality or said three-dimensional surface image; then (F) using said reference line or reference plane to delineate the margin of the disc cupping in said surface image; then (G) determining shape information of said portion from said three-dimensional surface image; and, from said shape information, (H) generating at least one three-dimensional point distribution model to classify said portion with respect to predetermined values reflecting retinal status.

2. The method as recited in claim 1, wherein step (E) further comprises fitting a first segment and a second segment of said layer in each image of said plurality with two straight lines, respectively, which lines intersect the margin of the optic disc, to obtain (i) a first reference point and second reference point at the intersection, respectively, and (ii) at least one of a reference line and a reference plane that, relative to the retina, is anterior to the first and second reference points, wherein the first and second segments of the layer are opposite each other on the optic disc in each image of said plurality.

3. A program that makes an information processing apparatus execute a method as recited in claim 1.

4. A computer-readable recording medium, comprising the program as recited in claim 3 recorded thereon.

5. The program as recited in claim 3, wherein the information process apparatus is a part of an imaging instrument.

* * * * *